United States Patent [19]

VandenBerg

[11] Patent Number: Plant 7,516

[45] Date of Patent: May 7, 1991

[54] CHRYSANTHEMUM PLANT NAMED CHANTAL

[75] Inventor: Cornelis P. VandenBerg, Salinas, Calif.

[73] Assignee: Yoder Brothers, Inc., Barberton, Ohio

[21] Appl. No.: 481,067

[22] Filed: Feb. 16, 1990

[51] Int. Cl.[5] ..... A01H 5/00

[52] U.S. Cl. ..... Plt./74

[58] Field of Search ..... Plt./74

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Chrysanthemum plant named Chantal particularly characterized by its flat capitulum form; daisy capitulum type; white ray floret color; diameter across face of capitulum of 25 to 28 mm when fully opened when grown as a pinched spray pot mum; very floriferous with excellent display of many small flowers; photoperiodic flowering response to short days of 45–50 days; plant height when grown as a pinched pot mum in a 15 cm pot of 18 to 25 cm; small, dark green foliage; spreading and very prolific branching pattern; and excellent tolerance to high temperatures for bud initiation and flower development.

3 Drawing Sheets

The present invention comprises a new and distinct cultivar of Chrysanthemum, botanically known as *Dendranthema grandiflora,* and referred to by the cultivar name Chantal.

Chantal, identified as 86-671001, was orignated by the inventor Cornelis P. VandenBerg from a cross made in a controlled breeding program in Salinas, Calif., in 1986.

The female parent of Chantal was an unnamed seedling identified as 83-538021, and described as a white daisy spray pot mum. The male parent of Chantal was an unnamed seedling identified as 83-S01002, and described as a white daisy spray pot mum with many very small flowers.

Chantal was discovered and selected as one flowering plant within the progeny of the stated cross by Cornelis P. VandenBerg in January 19787, in a controlled environment in Salinas, Calif.

The first act of asexual reproduction of Chantal was accomplished when vegetative cuttings were taken from the initial selection in March 1987 in a controlled environment in Salinas, Calif., by technicians working under the supervision of Cornelis P. VandenBerg.

Horticultural examination of controlled flowerings of successive plantings has shown that the unique combination of characteristics as herein disclosed for Chantal are firmly fixed and retained through successive generations of asexual reproduction.

Chantal has not been observed under all possible environmental conditions. The phenotype may vary significantly with variations in environment such as temperature, light intensity and daylength.

The following observations, measurements and comparisons describe plants grown in Salinas, Calif., and Leamington, Canada, under greenhouse conditions which approximate those generally used in commercial greenhouse practice.

The high temperature tolerance was determined in a controlled environment in Salinas, Calif., where temperatures were maintained at 35 degrees Celsius during the day and 24 degrees Celsius during the night for the duration of the crop.

The following traits have been repeatedly observed and are determined to be basic characteristics of Chantal, which, in combination, distinguish this Chrysanthemum as a new and distinct cultivar:

1. Flat capitulum form.
2. Daisy capitulum type.
3. White ray floret color.
4. Diameter across face of capitulum of 25 to 28 mm when fully opened, when grown as a pinched spray pot mum.
5. Very floriferous, with an excellent display of many small flowers.
6. Photoperiodic flowering response to short days of 45 to 50 days when flowered in Salinas, Calif., under normal greenhouse temperatures (15 degrees Celsius minimum night, 25 degrees Celsius maximum day).
7. Plant height of 18 to 15 cm from soil line when grown as a pinched pot mum with four cuttings in a 15 cm pot under normal greenhouse conditions in Salinas, Calif., with 14 to 15 long days after sticking unrooted cuttings prior to start of short days and 0 to 1 applications of 2500 ppm B-9 SP.
8. Small, dark green foliage.
9. Branching pattern is spreading and very prolific, each plant having 6 to 8 laterals after pinch.
10. Excellent tolerance to high temperatures for bud initiation and flower development.

The accompanying photographic drawings show typical inflorescence and leaf characteristics of Chantal, with the colors being as nearly true as possible with illustrations of this type.

Sheet 1 is a color photograph of Chantal grown as a pinched spray pot mum grown in a 10 cm pot.

Sheet 2 is a black and white photograph of three views of the inflorescence of Chantal.

Sheet 3 is a black and white photograph showing the upper and under sides of the leaves of Chantal at three stages of development (mature, intermediate and immature).

No commercial cultivar known to the invention can be compared with Chantal. The combination of white flower color, very high number of small flowers, small dark green foliage and spreading and very prolific branching pattern is unique, and is not represented in any commercial cultivar known to the inventor.

In the following description color references are made to The Royal Horticultural Society Colour Chart. The clear white ray floret color of Chantal is not represented in the R.H.S. Colour Chart. The color values were determined on plant material grown as a pinched spray pot mum in Salinas, Calif., on Aug. 28, 1989.

Classification:

*Botanical.*—*Dendranthema grandiflora* cv Chantal.

*Commercial.*—Daisy spray pot mum.

Inflorescence

A. Capitulum:

*Form.*—Flat.

*Type.*—Daisy.

*Diameter across face.*—From 25 to 28 mm when fully opened.

B. Corolla of Ray Florets:

*Color (generall tonality from a distance of three meters)*—White.

*Color (upper surface)*—White.

*Color (under surface)*—White.

*Shape.*—Straight, oblong, concave.

C. Corolla of Disc Florets:

*Color (mature)*—Closest to 12A.

*Color (immature)*—Closest to 7A.

D. Reproductive Organs:

*Androecium.*—Present on disc florets only; moderte pollen.

*Gynoecium.*—Present on both ray and disc florets.

PLANT

A. General Appearance:

*Height.*—Plant height of 18 to 25 cm from soil line when grown as a pinched pot mum with four cuttings in a 15 cm pot under normal greenhouse conditions in Salinas, Calif., with 14 to 15 long days after sticking unrooted cuttings prior to start of short days and 0 to 1 applications of 2500 ppm B-9 SP.

B. Foliage:

*Color (upper surface)*—147A.

*Color (under surface)*.13 147B.

*Shape.*—See photograph.

I claim:

1. A new and distinct Chrysanthemum plant named Chantal, as described and illustrated.

* * * * *

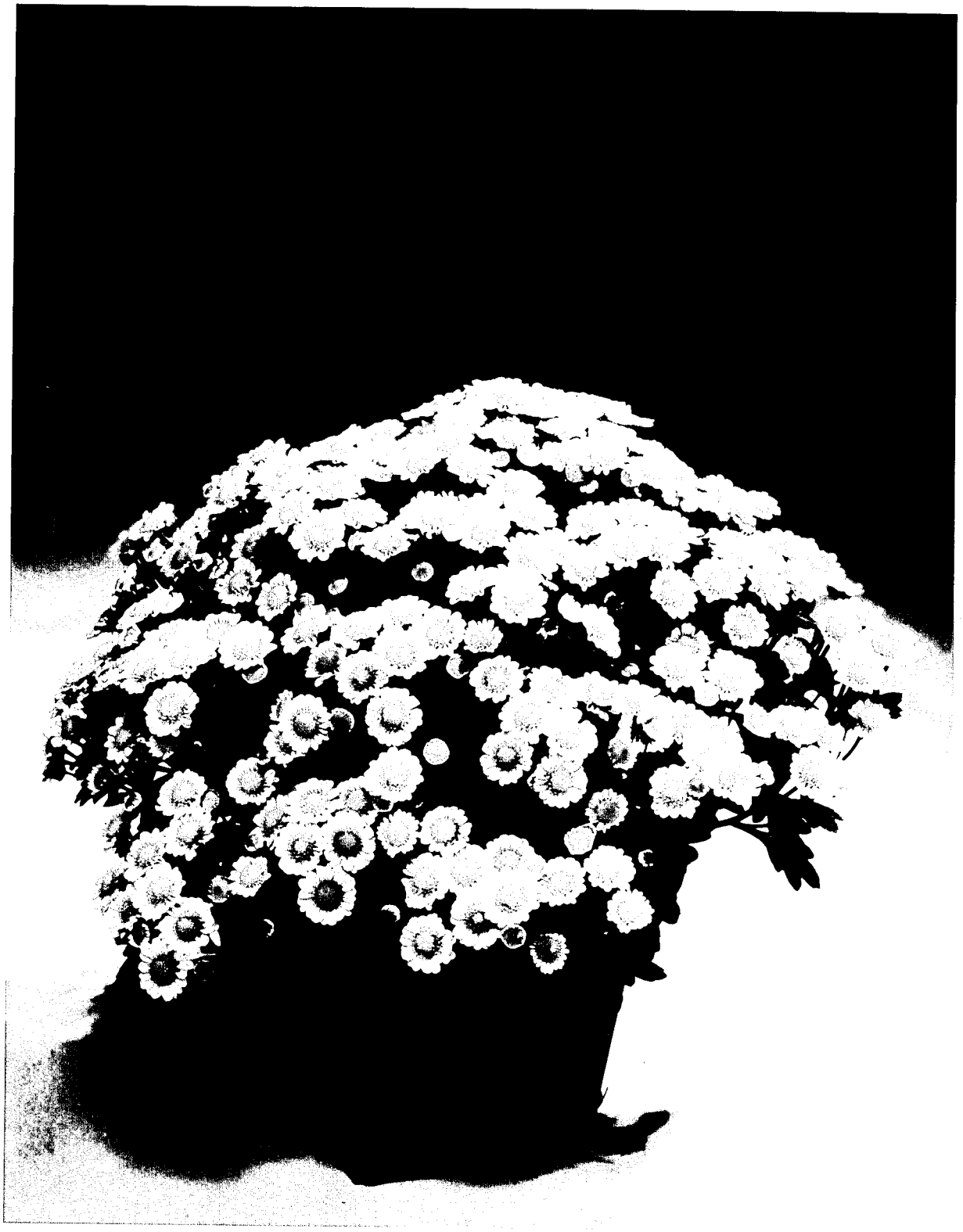

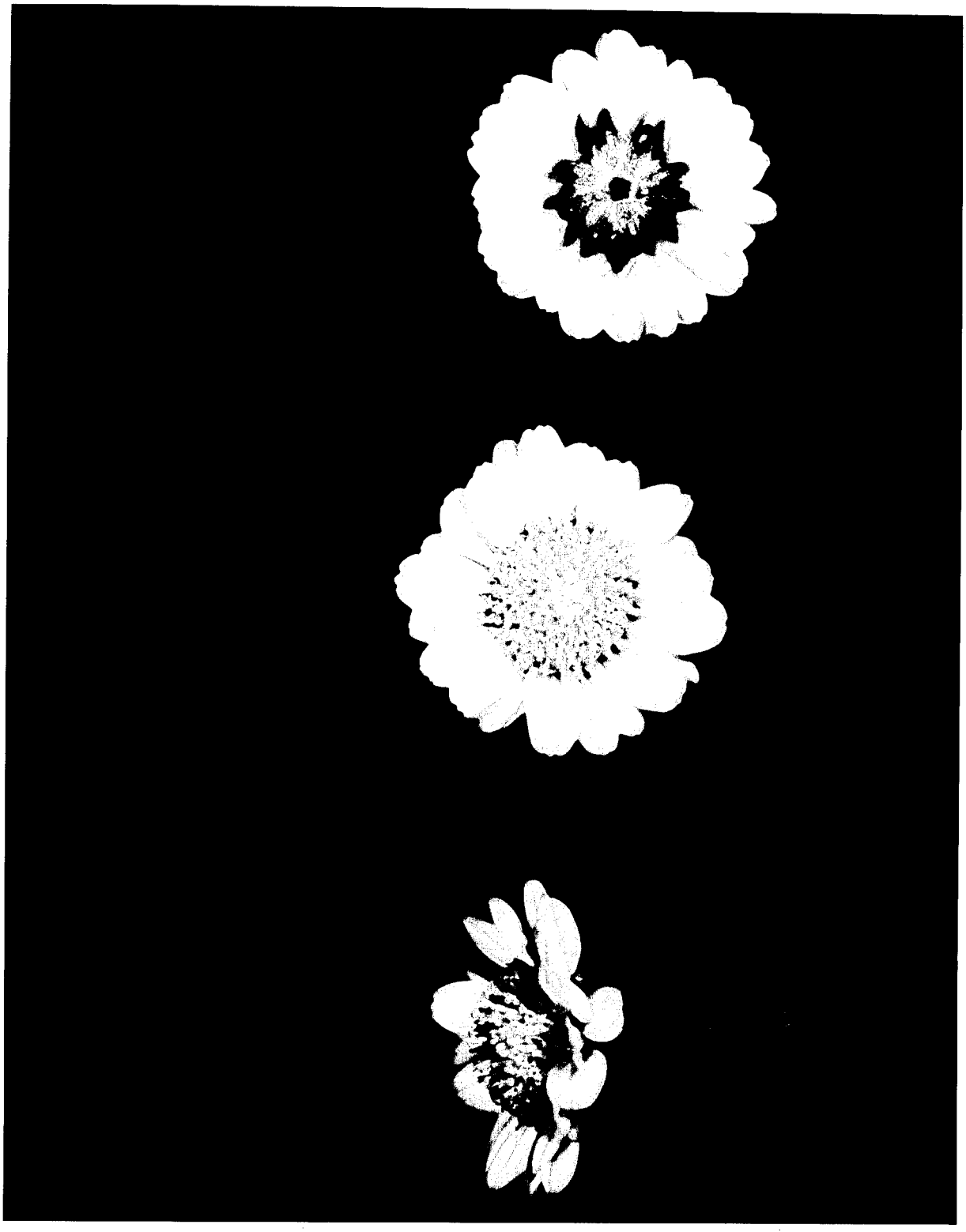

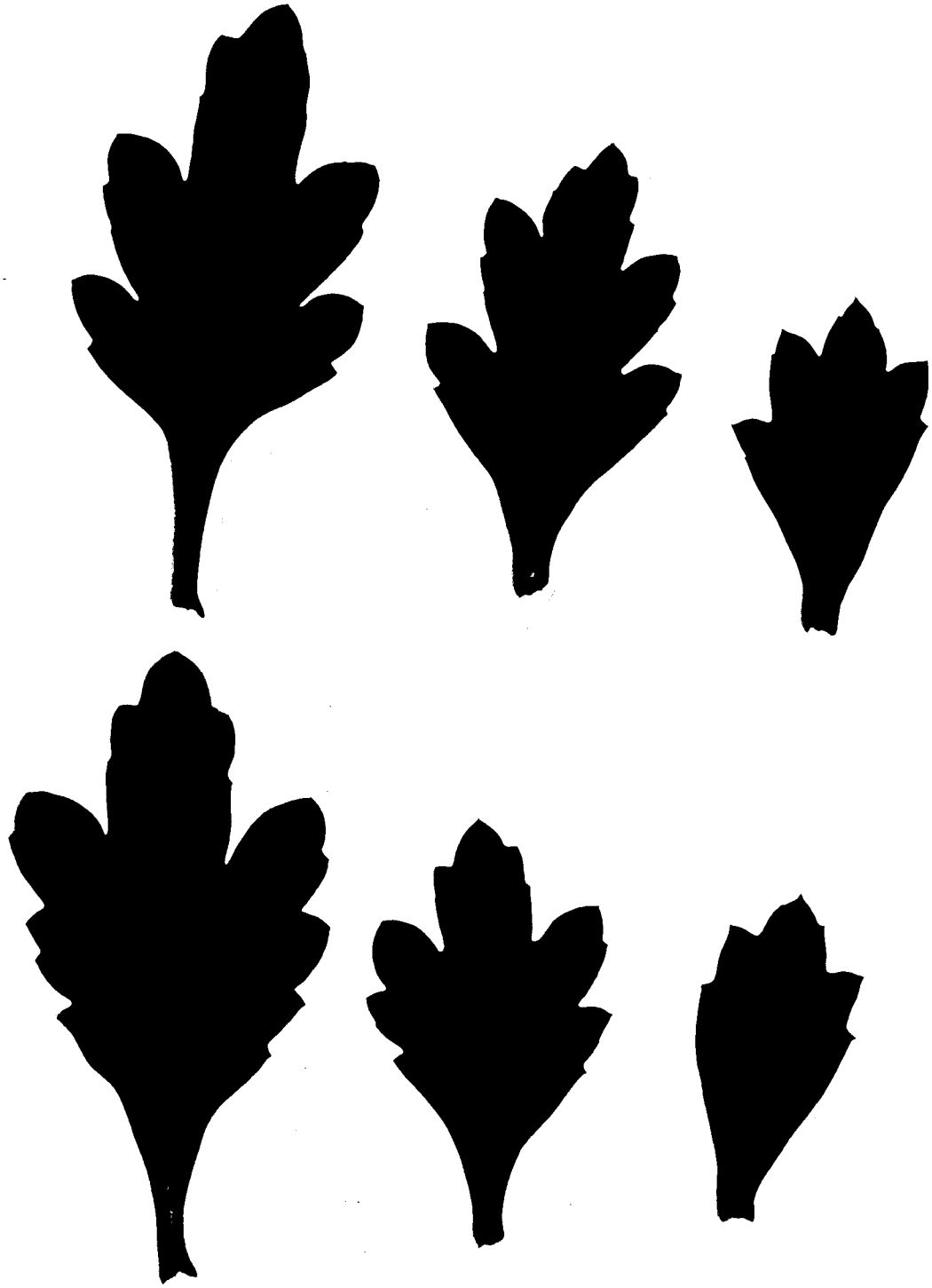

UNITED STATES PATENT AND TRADEMARK OFFICE

CERTIFICATE OF CORRECTION

PATENT NO. : PP 7,516

DATED : May 7, 1991

INVENTOR(S) : Cornelis P. VANDENBERG

It is certified that error appears in the above-identified patent and that said Letters Patent is hereby corrected as shown below:

Column 1, line 17: Change "19707" to --1987--.

Column 2, line 15: Change "13 to 15" to --13 to 25--.

Column 2, line 39: Change "invention" to --inventor--.

Column 4, line 19: Change "13 147B" to --147B--.

Signed and Sealed this

Fifth Day of July, 1994

*Attest:*

*Attesting Officer*

Bruce Lehman

BRUCE LEHMAN

*Commissioner of Patents and Trademarks*